US006359090B1

(12) United States Patent
Angeletakis

(10) Patent No.: US 6,359,090 B1
(45) Date of Patent: Mar. 19, 2002

(54) POLYMERIZABLE DISPERSANT

(75) Inventor: Christos Angeletakis, Orange, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 09/573,752

(22) Filed: May 18, 2000

Related U.S. Application Data

(63) Continuation-in-part of application No. 09/306,628, filed on May 6, 1999, now Pat. No. 6,300,390, which is a continuation-in-part of application No. 09/093,778, filed on Jun. 9, 1998, now Pat. No. 6,127,450.

(51) Int. Cl.[7] .......................... A61K 6/083; C09S 3/00; C08F 130/02
(52) U.S. Cl. ........................ 526/277; 523/116; 523/117; 523/205; 524/700; 433/228.1
(58) Field of Search .................... 523/116, 117, 523/205, 206; 524/700; 526/277; 433/228.1

(56) References Cited

U.S. PATENT DOCUMENTS

| 3,859,421 A | 1/1975 | Hucke |
| 4,407,984 A | 10/1983 | Ratcliffe et al. |
| 4,544,683 A | 10/1985 | Müller et al. |
| 4,647,638 A | * 3/1987 | Yokoshima et al. ......... 526/277 |
| 4,722,947 A | 2/1988 | Thanawalla et al. |
| 4,745,138 A | 5/1988 | Thanawalla et al. |
| 4,813,875 A | 3/1989 | Hare |
| 4,846,165 A | 7/1989 | Hare et al. |
| 4,952,613 A | 8/1990 | Hosoda |
| 4,957,554 A | 9/1990 | Mathers et al. |
| 5,125,971 A | 6/1992 | Nonami et al. |
| 5,134,175 A | 7/1992 | Lucey |
| 5,180,757 A | 1/1993 | Lucey |
| 5,399,782 A | 3/1995 | Leppard et al. |
| 5,534,559 A | 7/1996 | Leppard et al. |
| 5,674,513 A | 10/1997 | Snyder, Jr. et al. |
| 5,760,102 A | 6/1998 | Hall et al. |
| 5,843,348 A | 12/1998 | Giordano |
| 5,847,025 A | 12/1998 | Moszner et al. |
| 5,849,270 A | 12/1998 | Podszun et al. |
| 5,861,445 A | 1/1999 | Xu et al. |

FOREIGN PATENT DOCUMENTS

WO    WO 98/36729    8/1988

* cited by examiner

*Primary Examiner*—Peter Szekely
(74) *Attorney, Agent, or Firm*—Wood, Heron & Evans, LLP

(57) ABSTRACT

A polymerizable monophosphate ester dispersant, a highly-filled nonaqueous suspension containing the polymerizable monophosphate ester dispersant, and a method for forming cured articles by copolymerization of the resin matrix and dispersant in the suspension. Inclusion of the dispersant in a suspension of resin and solid particulate material enables an increase in the solid loading, which results in reduced shrinkage, a lower coefficient of thermal expansion and generally improved physical properties in an article cured therefrom.

21 Claims, No Drawings

POLYMERIZABLE DISPERSANT

CROSS REFERENCE TO RELATED APPLICATION

This application is a continuation-in-part of U.S. patent application Ser. No. 09/093,778 filed Jun. 9, 1998, now U.S. Pat. No. 6,127,450 and entitled DENTAL RESTORATIVE COMPOSITE, which is incorporated by reference herein in its entirety, and a continuation-in-part of U.S. patent application Ser. No. 09/306,628 filed May 6, 1999, now U.S. Pat. No. 6,300,390 and entitled DENTAL RESTORATIVE COMPOSITE, which is incorporated by reference herein in its entirety.

FIELD OF THE INVENTION

This invention relates to polymerizable dispersants, and more specifically, to phosphate-based ester dispersants that are effective in nonaqueous filled suspensions due to polymerizable groups that strengthen the composite after polymerization.

BACKGROUND OF THE INVENTION

High mechanical forces are required to incorporate solids into liquid media. To reduce the required dispersing forces, it is known to use dispersants, which facilitate the incorporation. Dispersants have been used in paints, molding compositions, coatings, plastic mixtures, printing inks, synthetic resin systems, and the like. The solids to be incorporated into the liquid media include, for example, pigments, fillers and fibers.

U.S. Pat. No. 5,151,218 discloses phosphoric acid ester dispersants of various structures. Recognized therein is the limited usefulness of certain structures as a dispersant in a broad number of applications. If a compound is not sufficiently compatible with the system, inadequate dispersion occurs due to insufficient interaction with the surrounding medium, and potentially precipitation phenomena with associated dulling, spotting and increased viscosity can occur. There is thus a need to develop dispersants that are broadly useful for wide-ranging applications.

In some applications, it is desirable to maximize the amount of solid in the suspension. For example, in a synthetic resin system, it may be desirable to limit the amount of the polymerizable resin and maximize the amount of filler, fiber or pigment material. The main factor limiting the volume fraction (load) of the solid in highly filled suspensions is particle-particle interactions. Dispersants, through their ability to reduce interactions between particles, can improve the flow (reduce the viscosity) of the suspension, thereby allowing a higher load. Dispersants in non-aqueous systems reduce particle interactions by a steric stabilization mechanism. A layer of the dispersant is adsorbed on the surface of the particles keeping them apart from one another, reducing the viscosity. The dispersant structure must contain a chain that allows for steric stabilization in the resin and it also must be strongly adsorbed on the particle surface. There is thus a further need to provide a dispersant that will be effective with a non-aqueous, highly filled suspension containing polymerizable resin.

SUMMARY OF THE INVENTION

The present invention provides a polymerizable monophosphate ester dispersant, a nonaqueous, highly-filled suspension containing the polymerizable monophosphate ester dispersant, and a method for forming cured articles by copolymerization of the resin matrix and dispersant in the suspension.

The dispersant of the present invention comprises a phosphate group, polyester group and polymerizable end group. The dispersant is trifunctional in nature. An exemplary dispersant of the present invention is a monophosphate ester according to the formula

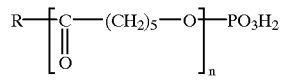

wherein R is a (meth)acrylate group radical or vinyl radical, and wherein n represents the number of units of caprolactone. Further exemplary embodiments include dispersants in which R is one of the following (meth)acrylate group radicals: oxyethyl methacryloyl-, oxyethyl acryloyl-, polyoxypropyl methacryloyl-, glyceryl dimethacryloyl-, and dipentaerythritol pentaacryloyl-. The inclusion of the dispersant, generally in an amount up to about 5 wt. %, in a suspension of resin and filler enables an increase in the filler loading, which results in reduced shrinkage, a lower coefficient of thermal expansion and generally improved physical properties in an article cured therefrom. These and other objects and advantages of the present invention shall become more apparent from the description of the preferred embodiments and the examples.

DETAILED DESCRIPTION

The present invention provides a class of phosphate based dispersants that are effective with nonaqueous, highly-filled suspensions. The dispersant is a trifunctional molecule that binds to the surface of a solid particulate material, reduces particle interactions by steric stabilization, and is copolymerizable with a resin matrix. Bonding with the surface of the solid, inorganic particulate material is accomplished with an anchoring phosphate group or ion. The phosphate ion has an affinity for the inorganic material. A spacer group, for example a polyester group, penetrates into the resin to promote steric stabilization. A polymerizable end group, either a monomer or copolymer, for example vinyl, methacrylate or acrylate, enables the dispersant to be copolymerized with the resin matrix. The presence of these groups in the dispersants of the present invention result in excellent compatibility with a broad range of resin systems, particularly (meth)acrylate-based (meaning methacrylate or acrylate) resin systems. Inclusion of the dispersants of the present invention into filled resin formulations will result in cured articles having lower shrinkage upon polymerization, lower coefficient of thermal expansion, and generally improved properties as compared to a formulation without the dispersant. In addition, copolymerization of the dispersant with the resin matrix provides improved bonding between solid particles and the resin matrix.

In one aspect of the present invention, inclusion of a novel dispersant in (meth)acrylate-based resin dental composite formulations results in increased filler loading and decreased viscosity, which after curing of the suspension provides a dental restorative with reduced shrinkage, a lower coefficient of thermal expansion and generally improved physical properties.

The dispersants of the present invention preferably comprise about 5 wt. % or less of the highly-filled suspensions, such as a dental composite paste. To obtain good uniformity of distribution of the dispersant in the final suspension, the dispersant is first mixed with the resin, followed by the slow addition of the solid particulate material, such as the inorganic glass fillers used in dental composites.

An exemplary dispersant of the present invention is a monophosphate ester of the formula

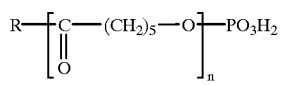

wherein R is a (meth)acrylate group radical or vinyl radical, and wherein n represents the number of units of caprolactone.

The presence of a carboxylic acid ester group of the dispersant results in excellent compatibility with (meth)acrylate-based resin systems. In exemplary embodiments, the dispersants of the present invention are monophosphate esters according to the above formula where R is one of the following (meth)acrylate group radicals:

Compound 1: R=oxyethyl methacryloyl

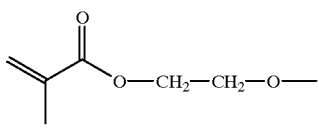

Compound 2: R=oxyethyl acryloyl

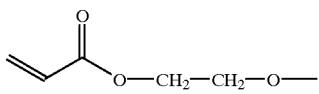

Compound 3: R=polyoxypropyl methacryloyl

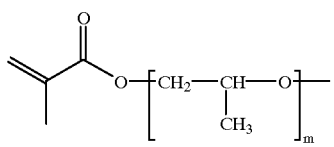

wherein m represents the number of units of oxypropyl.

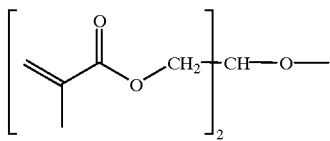

Compound 5: R=dipentaerythritol pentaacryloyl

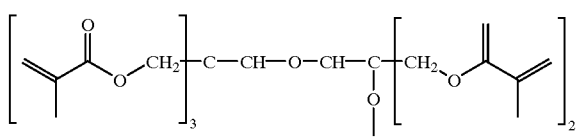

Compound 6: R=polyoxyethyl methacryloyl

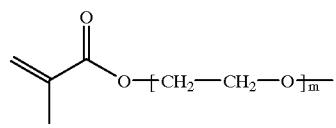

wherein m represents the number of units of oxyethyl.

Each of Compounds 1–6 may be prepared in two steps. In the first step, the hydroxy functional methacrylate is condensed with caprolactone under ring-opening polymerization conditions in the presence of catalytic amounts of $SnCl_2$ to prepare a polyester. In the second step, the polyester is reacted with polyphosphoric acid (117.5% concentration) at 65° C. to produce the phosphoric acid (monophosphate) ester. By way of example, the reaction sequence is shown below for the preparation of the hydroxyethyl methacrylate (HEMA) derivative Compound 1; it should be noted that substantially the same steps and conditions would be utilized to prepare any of Compounds 1–6:

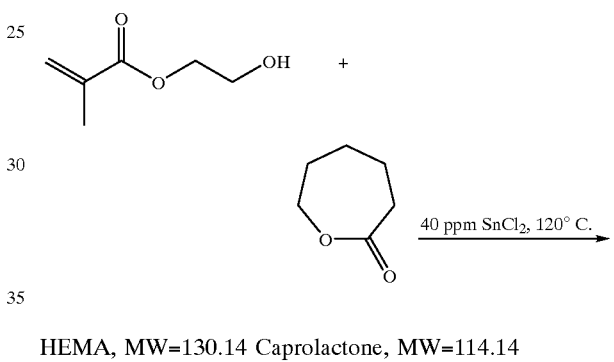

HEMA, MW=130.14 Caprolactone, MW=114.14

Polycaprolactone-modified HEMA

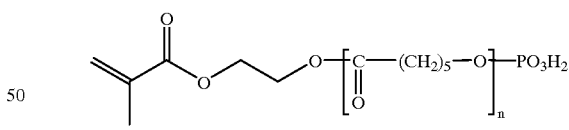

Compound 1: Polycaprolactone-modified HEMA Phosphate

The following examples are intended to further illustrate the present invention, and by no means should be interpreted to limit the scope of the present invention as claimed below.

EXAMPLE 1

In a 4-neck reaction kettle containing an air flow tube, a thermocouple, a condenser and a stirrer, 26.0 parts by weight of hydroxyethyl methacrylate (HEMA) were combined with 114.1 parts by weight of caprolactone, 0.14 parts by weight of methyl ether of hydroquinone (MEHQ) and 0.007 parts by weight of stannous chloride under a flow of dry air. The mixture was thermostated at 120° C. and stirring was-continued for 18 hours. The disappearance of the caprolactone was monitored with HPLC (High Pressure Liquid Chromatography) using a reverse phase column with 70/30 acetonitrile/water as eluant. The resultant liquid polycaprolactone-modified HEMA was essentially colorless.

In a three neck flask equipped with a stirrer and a condenser under a constant flow of dry air, 70.0 grams of the above product (polycaprolactone-modified HEMA) was combined with 8.45 grams of 117.5% phosphoric acid. The mixture was heated with stirring for 4 hours at 70° C. A light yellow oil resulted. Titration with 0.1N NaOH showed that the monophosphate ester was formed.

Various methacrylate derivatives prepared using the above procedures are listed in Table 1.

TABLE 1

Polycaprolactone-Modified Methacrylate Monophosphates

| Compound | Starting Material | Caprolactone: starting material (mole ratio) | Molecular Weight Average |
|---|---|---|---|
| 1a | Hydroxyethyl Methacrylate (HEMA) | 1:1 | 324 |
| 1b | HEMA | 2:1 | 438 |
| 1c | HEMA | 5:1 | 780 |
| 1d | HEMA | 7:1 | |
| 2 | Hydroxyethyl acrylate (HEA) | 5:1 | 766 |
| 3 | Polypropylene glycolmethacrylate (PPGMA) | 2:1 | 713 |
| 4a | Glycerol Dimethacrylate (GDMA) | 2:1 | 536 |
| 4b | GDMA | 5:1 | 879 |
| 5a | Dipentaerythritol pentaacrylate (DPEPA) | 2:1 | 713 |
| 5b | DPEPA | 5:1 | 1175 |
| 6a | Polyethyleneglycol methacrylate (PEGMA) | 2:1 | 678 |
| 6b | PEGMA | 5:1 | 1021 |

COMPOUND CHARACTERIZATION

A) 31P NMR Spectroscopy

Phosphate esters are difficult to analyze with 31P nuclear magnetic resonance (NMR) spectroscopy because usually only broad and ill-defined resonances are observed. Conversion to their corresponding trimethylsilyl (TMS) esters greatly improves the spectra by increasing the chemical shift differences between phosphoric acid, mono, di, and triester species and increasing the sharpening of all resonances considerably.

Samples of the reaction mixtures were initially dissolved in deuterochloroform followed by excess of N, O-bis(trimethylsilyl) trifluoroacetamide. Proton decoupled spectra were obtained at 162 MHz using 85% phosphoric acid as an external reference. The addition of trimethylsilyl groups causes an upfield shift of 9 ppm for each group added (see D. G. Anderson et al., "Hydrolytic Stability of Phosphate Ester Surfactants", Pesticide Formulations and Application Systems: 17th Volume, ASTM STP 1328 (G. R. Goss et al., eds., American Society for Testing and Materials 1997)). Using this technique, some of the phosphate esters were characterized as indicated in Table 2.

TABLE 2

Phosphate Ester Distributions in Weight Percent

| Compound | 1c | 4b | 6a | 6b |
|---|---|---|---|---|
| Diester | 10.4 | 12.1 | 16.1 | 16.8 |
| Monoester | 84.9 | 81.9 | 78.4 | 79.6 |
| Phosphoric acid | 4.4 | 4.8 | 4.6 | 3.1 |
| Pyrophosphoric acid | 0.3 | 1.1 | 0.8 | 0.6 |

Inspection of Table 2 shows that the monoester is the main product of the reaction and the amount of phosphoric acid remaining is under 5 wt. % and the amount of pyrophosphoric acid remaining is under 2 wt. %.

B) 1H NMR Spectroscopy

1H NMR spectra were obtained of Compound 1c and 4c dispersants in deuterochloroform at 400 MHz using TMS as reference. The following were observed in each case at the appropriate integral ratios: Ethylenic protons at 5.6 and 6.1 ppm, methyl at 1.9 ppm (methyl group attached to vinyl carbon) and multiplets of methylenes within the following regions: 1.3 to 1.8 ppm (attached to methylene only), 2.25 to 2.4 ppm (attached to carbonyl group), and 4.0 to 4.5 ppm (attached to ester oxygen).

C) Mass Spectroscopy

Flow injection (electrospray) mass spectrometry was used to characterize Compound 1b, 1c and 1d dispersants. The compounds were dissolved in 50:50 water:acetonitrile at a concentration of 2.5 mg/ml and each run by flow injection at 10 microliters/minute. Spectra were acquired on a Fisons VG Platform single quadrupole mass spectrometer (Bay Bioanalytical Laboratory, Richmond, Calif.). Negative ions were observed for these compounds using a capillary voltage of 3.22 kV and an extraction cone voltage of 42 kV. Source temperature was 80° C. The spectra of all 3 compounds show one series of ions for each separated by 114 mass units. The series with masses at 323.22, 437.31, 551.28, 665.37, 779.59, 893.80, and 1007.89 are the M-1 ions of the molecules with 1 to 7 caprolactone units attached. Prostaglandin $E_1$ (3-hydroxy-2-(3-hydroxy-1-octenyl)-5-oxocyclopentaneheptanoic acid) was run as a mass calibration check before and after the samples.

By way of example and not limitation, all of the above compounds may be used as dispersants in highly filled glass suspensions containing methacrylate resins for use as dental restorative composites. Nine test samples (test samples 1–9) were prepared according the following method. A methacrylate resin, as described in Table 3, was introduced into a planetary mixer and thermostated to 50° C.

TABLE 3

Resin Composition

| | |
|---|---|
| BisGMA (Bisphenol A Diglycidyl ether dimethacrylate) | 3.0 wt. % |
| Triethylene Glycol Dimethacrylate | 24.7 wt. % |
| Ethoxylated Bisphenol A Dimethacrylate | 71.1 wt. % |
| 2-Ethylhexyl-4-(dimethylamino)benzoate | 0.49 wt. % |
| Camphorquinone | 0.17 wt. % |
| 2-Hydroxy-4-methoxy Benzophenone | 0.49 wt. % |
| (BHT) Butylated Hydroxytoluene | 0.05 wt. % |
| Total | 100 |

A monophosphate ester with the structure described by the general formula above was then added to the resin so as to comprise 1.5 wt. % of the total resin/filler mixture with an 80 wt. % filler loading. The mixer was started for a few minutes to mix the resin phase and then the filler containing the physically admixed components listed in Table 4 was slowly added over a period of about 3 hours.

TABLE 4

| Filler Composition | |
|---|---|
| Barium Aluminum Borosilicate, silanated | 91.4 wt. % |
| 20 nm[1] Hydrophobic fumed silica (TS-530)[2] | 4.3 wt. % |
| 40 nm[1] Fumed Silica, silanated (OX-50)[3] | 4.3 wt. % |
| Total | 100 |

[1]average particle size
[2]Degussa Corp., Ridgefield Park, N.J.
[3]Degussa Corp., Ridgefield Park, N.J.

Mixing was continued for another hour and the resultant paste was deaerated under attenuated oxygen pressure. Table 5 details the physical properties of the test sample pastes (1–9) prepared along with the properties of control sample 1. All measurements were carried out using standard ISO methods except where indicated, and the standard deviations are provided in parentheses.

TABLE 6

| Compound 1c at Various Loadings | | | | |
|---|---|---|---|---|
| | Test Sample 3 | Test Sample 10 | Test Sample 11 | Test Sample 12 |
| Wt. % Compound 1c dispersant | 1.5 | 1.5 | 2.0 | 3.0 |
| Wt. % Filler Load | 80 | 76 | 82 | 82 |
| Penetrometer (mm) 0 g, (Flathead, 1 mm) | >8.0 | — | 4.4(0.2) | >8.0 |
| Penetrometer (mm) 0 g, (Flathead, 2 mm) | 6.6(0.0) | 4.6(0.2) | 2.0(0.2) | 5.1(0.0) |
| Depth of Cure at 600 mw/cm2, 4 mm diameter | 4.6(0.1) | 4.8(0.1) | 4.5(0.1) | 4.2(0.1) |
| % Volumetric Shrinkage | 2.60(0.18) | 2.91 (0.4) | 2.37(0.08) | 2.50(0.25) |
| Rockwell Hardness 15T | 83.4(0.1) | 80.9 (0.5) | 84.7(0.4) | 82.2(0.2) |

TABLE 5

| Physical Properties of Pastes Prepared with Various Dispersants | | | | | | | | | | |
|---|---|---|---|---|---|---|---|---|---|---|
| | Control Sample 1 | Test Sample 1 | Test Sample 2 | Test Sample 3 | Test Sample 4 | Test Sample 5 | Test Sample 6 | Test Sample 7 | Test Sample 8 | Test Sample 9 |
| Dispersant, 1.5 Wt. % | None | 1b | 1c | 1d | 2 | 3 | 4a | 4b | 5a | 5b |
| Wt % Filler Load (Vol. % Load) | 77 | 80 | 80 | 80 | 80 | 80 | 80 | 80 | 80 | 80 |
| Depth of Cure at 600 mw/cm², 4 mm diameter | 4.7 (0.1) | 4.2 (0.1) | 4.6 (0.1) | 4.0 (0.1) | 4.2 (0.1) | 3.9 (0.03) | 4.4 (0.1) | 4.1 (0.3) | 4.1 (0.1) | 4.5 (0.2) |
| Rockwell Hardness (15T)[1] | 79.7 (0.6) | 84.4 (0.38) | 83.4 (0.1) | 82.4 (0.3) | 83.3 (0.3) | 83.1 (0.3) | 84.0 (0.5) | 83.9 (0.1) | 83.6 (0.4) | 83.3 (0.1) |
| Compressive Strength (MPa) | 379 (20) | 290 (62) | 399 (21) | 375 (17) | 314 (29) | 341 (29) | 394 (43) | 408 (34) | 387 (27) | 381 (27) |
| Flexural Strength (MPa) | 137 (23) | 124 (22) | 129 (12) | 120 (9) | 127 (14) | 110 (11) | 114 (22) | 125 (26) | 105 (12) | 106 (6) |
| Flexural Modulus (MPa) | 10,192 (599) | 11,362 (773) | 11,189 (968) | 10,827 (1,035) | 12,187 (1,754) | 11,460 (1,045) | 11,977 (899) | 10,571 (2,051) | 12,404 (1,006) | 11,664 (619) |
| Penetrometer (mm)[2] 0 g, (Needle, 1 mm) | 4.2 (0.1) | 3.6 (0.1) | >8.0 | >8.0 | >8.0 (0.1) | 5.5 (0.2) | 2.1 (0.2) | 6.2 (0.2) | 2.7 (0.1) | 3.0 |
| Penetrometer (mm)[3] 0 g, (Flathead, 1 mm) | 2.8 (0.2) | 2.3 (0.2) | >8.0 | >8.0 | 7.1 (0.1) | 2.3 (0.1) | 1.3 (0.1) | 4.3 (0.1) | 1.5 (0.1) | 1.0 (0.1) |
| Penetrometer (mm)[3] 0 g, (Flathead, 2 mm) | | | | 5.7 (0.1) | 4.5 (0.1) | | | | | |

[1]Average of 3 measurements on the surface of a cylindrical sample 10 mm in diameter and 4 mm in height. The samples were light cured for 40 seconds, and stored in water for 24 hours at 37° C. prior to measurement.
[2]Precision Penetrometer (GCA Corp., Chicago, IL) with a 1 mm needle was used with no additional weight (0 g). The paste was placed in a mold 10 mm in diameter and 8 mm in height. Penetration was performed for 10 seconds. An average of 3 measurements is reported.
[3]Same test as above, but using a flat head rather than a needle, to simulate the effect of the impact from dental instruments having a flat head on the composite.

The properties shown in Table 5 demonstrate that there is a dramatic reduction of viscosity of the pastes where the monophosphate esters of Compound 1 are included. The penetrometer test is indicative of the viscosity of the paste, although not directly related. The addition of a dispersant of the present invention enabled the higher filler loading of 80 wt. % as compared to the maximum achievable loading of 77 wt. % in the control paste not containing a dispersant. Furthermore, the physical properties of the composites are not significantly reduced by the addition of the polycaprolactone-modified methacrylate monophosphates.

As a further comparison, the most efficient dispersant listed above, Compound 1c, was also formulated in pastes at different loads and amounts (test samples 10–12). The results of test samples 3 and 10–12 are listed in Table 6.

TABLE 6-continued

| Compound 1c at Various Loadings | | | | |
|---|---|---|---|---|
| | Test Sample 3 | Test Sample 10 | Test Sample 11 | Test Sample 12 |
| Compressive Strength (MPa) | 399(21) | 350(28) | 312(48) | 274(25) |
| Flexural Strength (MPa) | 129(12) | 139(13) | 132(17) | 105(14) |
| Flexural Modulus (MPa) | 11,189 (968) | 12,297 (727) | 12,159 (1,038) | 10,471 (741) |

The results shown in Table 6 demonstrate that a low relative viscosity paste having acceptable physical properties may be prepared at 82 wt. % filler loading with only 2 wt. % dispersant based on a 1c Compound. In contrast, pastes incorporating no dispersant cannot be made with a filler loading above 77 wt. %. See Control Sample 1 in Table 5.

While (meth)acrylate polymerizable end groups have been discussed in detail above, it is to be understood that other polymerizable end groups may be used to achieve copolymerization of the dispersant with the resin matrix. An appropriate polymerizable end group may be selected for compatibility with a given resin system. The end group in a dispersant of the present invention may be unsaturated. Representative types of end groups are vinyl and (meth) acryloyl.

Also, while dental filler particulate has been described in detail above, it is to be understood that other solid inorganic materials may be incorporated into resin systems with the aid of a dispersant of the present invention. Such solid inorganic materials may include, among others, pigments and fibers.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, the dispersant of the present invention may be added to any resin/filler mixture, not just dental composite systems. Moreover, other polymerizable groups may be selected for copolymerization. The invention in its broader aspects is therefore not limited to the specific details, representative method and illustrative examples shown and described. Accordingly, departures may be made from such details without departing from the scope or spirit of applicant's general inventive concept.

What is claimed is:

1. A polymerizable dispersant for use in nonaqueous, filled suspensions comprising:

a polycaprolactone-modified monophosphate ester of the formula

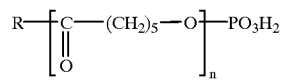

wherein R is a (meth)acrylate group radical or vinyl radical and n represents the number of units of caprolactone, and wherein the monophosphate ester is selected from the group consisting of:
(a) polycaprolactone-modified polypropylene glycol-methacrylate phosphate prepared from a mole ratio of caprolactone:polypropylene glycolmethacrylate of 2:1,
(b) polycaprolactone-modified glycerol dimethacrylate phosphate prepared from a mole ratio of caprolactone:glycerol dimethacrylate of 2:1,
(c) polycaprolactone-modified glycerol dimethacrylate phosphate prepared from a mole ratio of caprolactone:glycerol dimethacrylate of 5:1,
(d) polycaprolactone-modified dipentaerythritol pentaacrylate phosphate prepared from a mole ratio of caprolactone:dipentaerythritol pentaacrylate of 2:1,
(e) polycaprolactone-modified dipentaerythritol pentaacrylate phosphate prepared from a mole ratio of caprolactone:dipentaerythritol pentaacrylate of 5:1,
(f) polycaprolactone-modified polyethyleneglycol methacrylate phosphate prepared from a mole ratio of caprolactone:polyethyleneglycol methacrylate of 2:1, and
(g) polycaprolactone-modified polyethyleneglycol methacrylate phosphate prepared from a mole ratio of caprolactone:polyethyleneglycol methacrylate of 5:1.

2. A nonaqueous suspension comprising:

a polymerizable resin; and solid inorganic particles dispersed in the resin, said particles at least partially coated with a dispersant comprising a phosphate group, a polyester group, and a polymerizable end group, wherein the resin and dispersant are copolymerizable.

3. The suspension of claim 2, wherein the resin is a (meth)acrylate resin and the polymerizable end group of the dispersant is a (meth)acrylate group.

4. The suspension of claim 2, wherein the suspension includes at least about 80 wt. % solid particles.

5. The suspension of claim 4, wherein the suspension includes less than about 5 wt. % dispersant.

6. The suspension of claim 2, wherein the dispersant is a polycaprolactone-modified methacrylate monophosphate.

7. The suspension of claim 2, wherein the polymerizable end group is a radical selected from the group consisting of: oxyethyl methacryloyl-, oxyethyl acryloyl-, polyoxypropyl methacryloyl-, glyceryl dimethacryloyl-, dipentaerythritol pentaacryloyl- and polyoxyethyl methacryloyl-.

8. A nonaqueous suspension comprising:

a polymerizable resin; and solid inorganic particles dispersed in the resin, said particles at least partially coated with a polymerizable dispersant comprising:

a polycaprolactone-modified monophosphate ester of the formula

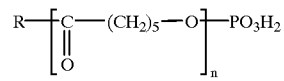

wherein R is a (meth)acrylate group radical or vinyl radical and n represents the number of units of caprolactone, and wherein the resin and dispersant are copolymerizable.

9. The suspension of claim 8, wherein the resin is a (meth)acrylate resin and R is a (meth)acrylate group.

10. The suspension of claim 8, wherein the suspension includes at least about 80 wt. % solid particles.

11. The suspension of claim 10, wherein the suspension includes less than about 5 wt. % dispersant.

12. The suspension of claim 8, wherein the dispersant is a polycaprolactone-modified methacrylate monophosphate.

13. The suspension of claim 8, wherein R is a radical selected from the group consisting of: oxyethyl methacryloyl-, oxyethyl acryloyl-, polyoxypropyl methacryloyl-, glyceryl dimethacryloyl-, dipentaerythritol pentaacryloyl- and polyoxyethyl methacryloyl-.

14. A method of making a highly-filled, cured article, comprising:

mixing a polymerizable resin and a polymerizable dispersant, wherein the polymerizable dispersant comprises a phosphate group, a polyester group, and a polymerizable end group;

mixing into the resin and dispersant an inorganic solid particulate material to form a paste containing at least about 80 wt. % of the particulate material; and copolymerizing the resin and dispersant to form a cured article.

15. The method of claim 14, wherein the paste includes less than about 5 wt. % dispersant.

16. The method of claim 14, wherein the resin is a (meth)acrylate resin and the dispersant is a polycaprolactone-modified methacrylate monophosphate.

17. The method of claim 14, wherein the polymerizable end group is a radical selected from the group consisting of: oxyethyl methacryloyl-, oxyethyl acryloyl-, polyoxypropyl methacryloyl-, glyceryl dimethacryloyl-, dipentaerythritol pentaacryloyl- and polyoxyethyl methacryloyl-.

18. A method of making a highly-filled, cured article, comprising:

mixing a polymerizable (meth)acrylate resin and a polymerizable dispersant, wherein the polymerizable dispersant comprises a polycaprolactone-modified monophosphate ester of the formula

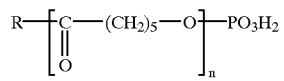

wherein R is a (meth)acrylate group radical and n represents the number of units of caprolactone;

mixing into the resin and dispersant an inorganic solid particulate material to form a paste containing at least about 80 wt. % of the particulate material; and copolymerizing the resin and dispersant to form a cured article.

19. The method of claim 18, wherein the paste includes less than about 5 wt. % dispersant.

20. The method of claim 18, wherein the dispersant is a polycaprolactone-modified methacrylate monophosphate.

21. The method of claim 18, wherein R is a radical selected from the group consisting of: oxyethyl methacryloyl-, oxyethyl acryloyl-, polyoxypropyl methacryloyl-, glyceryl dimethacryloyl-, dipentaerythritol pentaacryloyl- and polyoxyethyl methacryloyl-.

* * * * *

UNITED STATES PATENT AND TRADEMARK OFFICE
CERTIFICATE OF CORRECTION

PATENT NO.      : 6,359,090 B1
DATED           : March 19, 2002
INVENTOR(S)     : Christos Angeletakis It is certified that error appears in the above-identified patent and that said Letters Patent is hereby corrected as shown below:

Column 3,
Line 50, "[missing text]" should be -- Compound 4: R = glyceryl dimethacryloyl --
Line 62, "CH" (second occurrence), should be -- $CH_2$ --.

Column 4,
Line 67, "was-continued" should be -- was continued --.

Column 6,
Line 29, "acetronitrile" should be -- acetonitrile --.
Line 48, "according the following" should be -- according to the following --.

Column 8,
Lines 45 and 46, (figures as printed are lined up incorrectly)
"Penetrometer $(mm)^2$ 0g, (Needle, 1mm) 4.2  3.6  >8.0 >8.0 >8.0  5.5  2.1  6.2  2.7  3.0
                                          (0.1) (0.1)              (0.1) (0.2) (0.2) (0.2) (0.1)"
should be
-- Penetrometer $(mm)^2$ 0g, (Needle, 1mm) 4.2  3.6  >8.0  >8.0  >8.0  5.5  2.1  6.2  2.7  3.0
                                          (0.1) (0.1)                  (0.1) (0.2) (0.2) (0.2) (0.1) --

Signed and Sealed this

Twenty-ninth Day of October, 2002

Attest:

JAMES E. ROGAN
Attesting Officer   Director of the United States Patent and Trademark Office